(12) United States Patent
Belkin

(10) Patent No.: US 8,662,388 B2
(45) Date of Patent: Mar. 4, 2014

(54) MEDICAL IDENTIFICATION SYSTEM AND METHOD OF IDENTIFYING INDIVIDUALS, MEDICAL ITEMS, AND ASSOCIATIONS THEREBETWEEN USING SAME

(75) Inventor: Anatoly S. Belkin, Glenview, IL (US)

(73) Assignee: Hospira, Inc., Lake Forest, IL (US)

(*) Notice: Subject to any disclaimer, the term of this patent is extended or adjusted under 35 U.S.C. 154(b) by 24 days.

(21) Appl. No.: 13/290,254

(22) Filed: Nov. 7, 2011

(65) Prior Publication Data

US 2012/0111938 A1    May 10, 2012

Related U.S. Application Data

(60) Provisional application No. 61/411,563, filed on Nov. 9, 2010.

(51) Int. Cl.
*G06K 5/00* (2006.01)
*G06Q 10/00* (2012.01)
*G06Q 50/00* (2012.01)
*G02F 1/1333* (2006.01)

(52) U.S. Cl.
USPC .............. 235/380; 705/2; 705/3; 349/86

(58) Field of Classification Search
USPC ................. 235/380; 705/2, 3; 349/86
See application file for complete search history.

(56) References Cited

U.S. PATENT DOCUMENTS

| | | | |
|---|---|---|---|
| 5,026,084 A | 6/1991 | Pasfield | |
| 5,261,702 A * | 11/1993 | Mayfield | 283/115 |
| 5,493,430 A * | 2/1996 | Lu et al. | 349/106 |
| 5,636,044 A * | 6/1997 | Yuan et al. | 349/142 |
| 5,931,764 A | 8/1999 | Freeman et al. | |
| 5,967,559 A * | 10/1999 | Abramowitz | 283/67 |
| 6,223,440 B1 | 5/2001 | Rashman | |
| 6,227,371 B1 * | 5/2001 | Song | 206/534 |
| 6,514,460 B1 | 2/2003 | Fendrock | |
| 6,753,830 B2 | 6/2004 | Gelbman | |
| 6,915,170 B2 | 7/2005 | Engleson et al. | |
| 6,924,781 B1 | 8/2005 | Gelbman | |
| 6,998,984 B1 | 2/2006 | Zittrain | |
| 7,017,293 B2 | 3/2006 | Riley | |
| 7,142,190 B2 * | 11/2006 | Martinez | 345/106 |
| 7,248,239 B2 | 7/2007 | Dowling | |
| 7,258,534 B2 | 8/2007 | Fathallah et al. | |
| 7,324,000 B2 | 1/2008 | Zittrain et al. | |

(Continued)

FOREIGN PATENT DOCUMENTS

| | | | |
|---|---|---|---|
| EP | 0564127 A3 | 6/1993 | |
| WO | 2009036327 A1 | 3/2009 | |

OTHER PUBLICATIONS

Electronic Skins, Reflex Electronic Skins Product Brief 25127B, Kent Displays, Inc., www.kentdisplays.com, 2009, USA.

(Continued)

*Primary Examiner* — Christle Marshall
*Assistant Examiner* — Claude J Brown
(74) *Attorney, Agent, or Firm* — Michael R. Crabb

(57) ABSTRACT

An assembly and method of identifying and visually associating individuals and medical equipment includes a computing device having a software algorithm that determines a unique combination of one or more human cognitive identifiers to avoid confusion and displays the determined selection on an electronic skin located on the individual or medical equipment so that identities and associations amongst individuals and equipment can be understood readily.

18 Claims, 3 Drawing Sheets

(56) References Cited

U.S. PATENT DOCUMENTS

| | | |
|---|---|---|
| 7,621,009 B2 | 11/2009 | Elhabashy |
| D606,533 S | 12/2009 | de Jong et al. |
| 7,687,678 B2 | 3/2010 | Jacobs |
| 2003/0047126 A1 | 3/2003 | Tomaschko |
| 2003/0059750 A1 | 3/2003 | Bindler et al. |
| 2004/0145480 A1* | 7/2004 | Despotis ............... 340/572.9 |
| 2005/0027560 A1* | 2/2005 | Cook ............................. 705/2 |
| 2005/0040226 A1* | 2/2005 | Al-Sheikh ................. 235/380 |
| 2006/0042139 A1 | 3/2006 | Mendes |
| 2006/0089855 A1 | 4/2006 | Holland et al. |
| 2006/0267753 A1 | 11/2006 | Hussey et al. |
| 2007/0016443 A1 | 1/2007 | Wachman et al. |
| 2007/0213598 A1 | 9/2007 | Howard et al. |
| 2007/0213657 A1 | 9/2007 | Jennewine et al. |
| 2007/0299695 A1* | 12/2007 | Jung et al. ..................... 705/3 |
| 2008/0065417 A1* | 3/2008 | Jung et al. ..................... 705/2 |
| 2008/0149117 A1 | 6/2008 | Raghuram |
| 2008/0172337 A1* | 7/2008 | Banfield et al. ............. 705/51 |
| 2008/0246748 A1 | 10/2008 | Cassidy et al. |
| 2009/0051560 A1 | 2/2009 | Manning et al. |
| 2009/0057399 A1 | 3/2009 | Sajkowsky |
| 2009/0135196 A1 | 5/2009 | Holland et al. |
| 2009/0231249 A1* | 9/2009 | Wang et al. ................... 345/83 |
| 2009/0275886 A1 | 11/2009 | Blomquist et al. |
| 2009/0284691 A1* | 11/2009 | Marhefka et al. ............ 349/86 |

OTHER PUBLICATIONS

Reflex Electronic Skins Engineering Evaluation Kit, Kent Displays, Inc. 25136A, www.kentdisplays.com, Mar. 10, 2009, USA.

K.-M. H. Lenssen, et al., Bright Color Electronic Paper Technology and Applications, IDW '09 Publication EP1-2 (Philips Research), pp. 529-532, 2009, The Netherlands.

Hospira GemStar Pain Management Infusion System 9-084-PR1-2-2, www.hospira.com/Products/gemstar_painmanagement.aspx, pp. 1-2, Jan. 28, 2010, Lake Forest, IL, USA.

* cited by examiner

MEDICAL IDENTIFICATION SYSTEM AND METHOD OF IDENTIFYING INDIVIDUALS, MEDICAL ITEMS, AND ASSOCIATIONS THEREBETWEEN USING SAME

CROSS REFERENCE TO RELATED APPLICATION

This application claims the benefit of U.S. Provisional Application No. 61/411,563 filed Nov. 9, 2010.

BACKGROUND OF THE INVENTION

This invention relates to a medical identification assembly. More specifically this invention relates to an assembly and method of utilizing an algorithm to correctly identify individuals, medical devices, other medical items, and associations therebetween in a medical setting.

In a typical hospital thousands of patients are admitted and taken care of by caregivers on a daily basis. Oftentimes patients can have similar names, diagnosis and prescriptions. Similarly when a patient is in surgery many caregivers can be in the operating room each using one or more medical devices or items to assist the patient. Sometimes these devices can be similar in style and all be attached to an IV pole or plugged into similar outlets. All of these similarities lead to confusion within the hospital. Prescriptions and medicines can be provided to an incorrect patient. In the heat of a surgery a caregiver can grab and utilize the wrong medical device causing time to be wasted and mistakes to be made.

In one attempt to address these concerns, hospitals have developed protocols in an attempt to insure confusion is minimal. Wristbands with patients' names and other identifiers such as bar codes are used. These wristbands have even been color coded to provide further information to a caregiver. Other solutions have also included using post-it notes on different medical devices and charts to help associate medicine with patients and machines with caregivers.

Despite these protocols and methods, mistakes still occur. Patients receive incorrect medicines and caregivers use incorrect medical devices, placing the patient in dangerous situations. Thus, a need in the art exists for a medical identification assembly and method of identifying an individual in a medical facility to correctly identify individuals, medical devices, other medical items, and associations therebetween in a medical setting that minimizes mistakes and cost.

Thus a principle object of the present invention is to provide a medical identification and association assembly that minimizes identification mistakes.

These and Other Objects, Features and Advantages Will become apparent from the specification and claims.

BRIEF SUMMARY OF THE INVENTION

A medical identification assembly and method of using the same is described herein. The assembly utilizes a computing device that has software with an algorithm that sorts through patient and/or caregiver information and determines a combination of human cognitive identifiers to associate with an individual such as a patient or caregiver. The combination of human cognitive identifiers is then placed on a medium to identify an individual.

In another aspect of the invention the assembly utilizes the computing device and software algorithm to sort through patient, caregiver, medical device or other medical item information and determine a combination of human cognitive identifiers to associate patients or caregivers with devices or other medical items for identification and control purposes.

DETAILED DESCRIPTION OF THE PREFERRED EMBODIMENT

Figure 1:
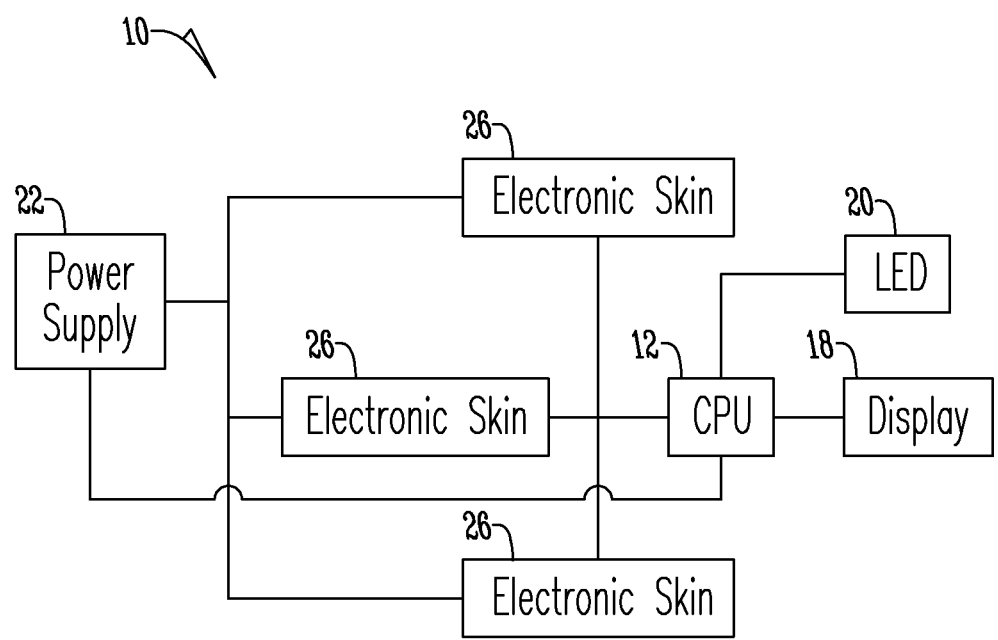
FIG. 1 is a system diagram of a medical identification assembly.

The figures show a medical identification assembly 10 having a computing device 12. While shown in the system diagram in FIG. 1 as a central processing unit the computing device 12 may be a controller, a microprocessor, a hand held device (optionally equipped with VERISCAN™ software available from Hospira, Inc. of Lake Forest, Ill., USA), or the like without falling outside of this disclosure. The computing device 12 has software 13 that utilizes an algorithm 14.

Computing device 12 is configured to receive and the algorithm 14 is able to sort through both patent and caregiver information and identify similarities of attributes of the patients and caregivers. For example, the algorithm 14 can identify when patients have the same or similar names, when patients have the same or similar diagnosis, are on the same floor of the hospital, are in the same wing or area of the hospital, have the same or similar birthdays, have the same doctor, nurse or other caregiver, or the like.

Then based on these similarities the algorithm 14 generates one or more identifiers 16 or a unique combination of human cognitive identifiers 16. Human cognitive human readable identifiers are identifiers that a person can instantly recognize such as a color or a shape. These identifiers 16 are not like a bar code that one must utilize a scanner to identify. Examples of human cognitive identifiers include, but are not limited to shapes, colors, fonts, line patterns, icons, shadings, symbols, backgrounds, borders and the like. Thus the algorithm 14 ensures that if a first patient named John Smith is identified by the color blue and a rectangular shape that a second patient named John Smith will not be identified with blue or color similar to blue, such as green, and will not be identified with a shape such as a rectangle or square. So the algorithm could choose a pink background with a triangular shaped icon for the second John Smith.

The computing device 12 also can have or be in communication with a display 18, utilize an LED 20 and can be powered by a power supply 22 such as a battery, electrical outlet or the like. The computing device 12 is electrically connected to and/or is in communication with devices 24 that can place the identifiers 16 on a medium 26. For example device 24 can be a color printer that generates prescription labels or generates wrist bands. Medium 26 can include but is not limited to wrist bands, badges, electronic skins, electronic medical records (EMR records), prescription labels and the like.

Figure 2:
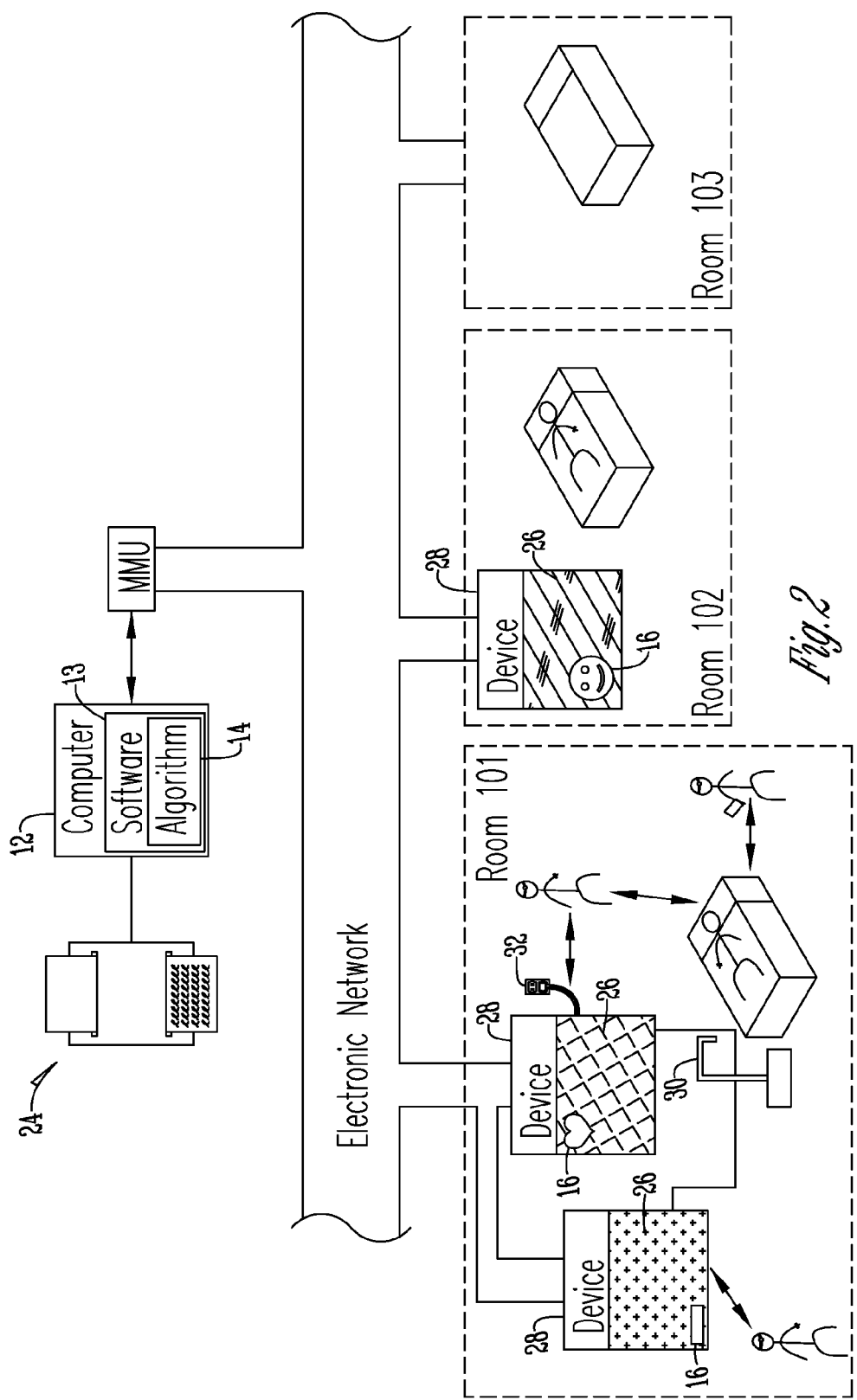
FIG. 2 is a schematic diagram of a medical identification assembly.
Figure 3:
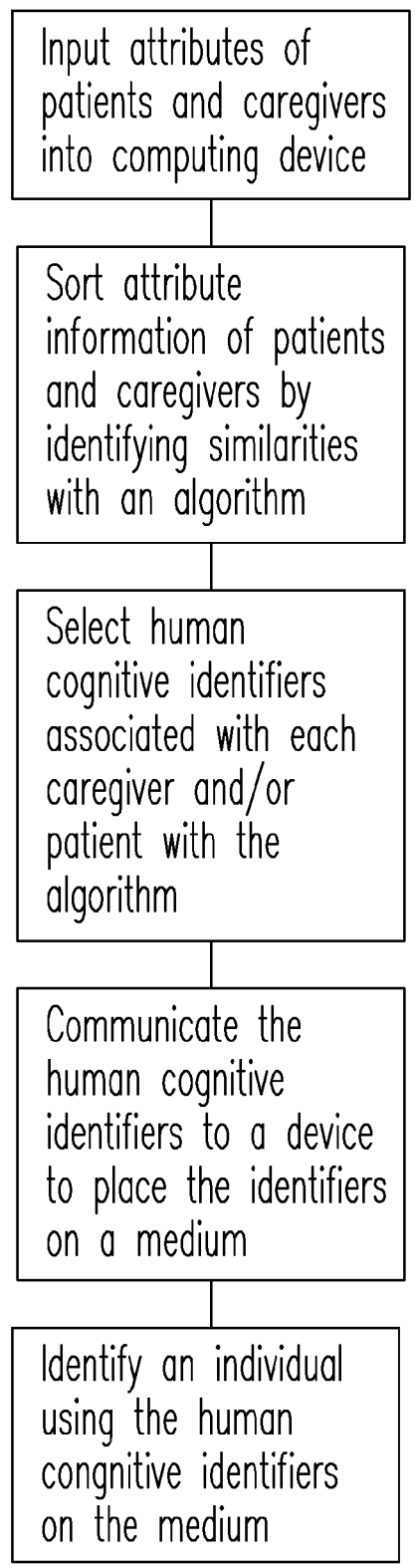
FIG. 3 is a flow chart of the method of identifying an individual in a medical facility.

In one embodiment the medium 26 is in communication with or electrically connected to the computing device 12. For example an electric skin is a type of flexible display that has electronic components that can be operated to present different images thereon. An example of an electric skin can be seen at http://www.kentdisplays.com/products/lcdelectronic-skins.html and is incorporated herein. The electric skin can be placed over a medical device 28, including but not limited to a medical pump, ventilator, patient-connected monitoring or diagnostic equipment and the like, such that the identifiers on the skin may be seen in three dimensions. The electric skin can be included on one or more visible surfaces of the medical device 28. By placing the electric skin on a plurality of surfaces that face in a plurality of directions, the skin can be seen from a variety of directions and viewing of the skin can be independent of the direction of the display 18. Thus in an embodiment, such as shown in FIG. 2, where a patient is being operated on and a plurality of caregivers are in an operating room, each having a medical device 28 that they attached to an IV pole 30 or plugged into a similar outlet 32, the electric skin provides an automatic cognitively recognized identification means for each medical device 28. This minimizes or even eliminates the chance of a caregiver mistakenly using another caregivers' medical device 28.

The electric skins or medium 26 can be associated with a plurality of medical devices 28 such that each medical device 28 has a unique identifier. Similarly the electronic skin 26 can be associated with a plurality of caregivers such that each caregiver has a unique identifier. Alternatively, the electric skins 26 can be associated with a plurality of patients such that each patient has a unique identifier.

Furthermore, by utilizing the same unique identifier patients, medical devices 28 and/or caregivers can be associated with each other in logical and easily visually discernible groups according to the present invention. For example, a plurality of electronic medical devices 28 can be associated with a single patient or caregiver by use of the same unique identifier. A plurality of patients can be associated with a single caregiver or medical device by use of the same unique identifier. For purpose of identification, control or authorization, a plurality of caregivers or medical devices can be associated with a single patient by use of the same unique identifier assigned to the patient. One advantageous feature of using an electronic skin on a medical device or wearable identification media is that the identifiers can be modified and reused as needed. For example, the electronic skin on a patient's wristband can be electronically controlled to change its identifier to correspond with an identifier on one or more medical devices or one or more caregivers it is brought into proximity with.

The computing or controlling device 12 controls the color/pattern of the skin 26 based on the context of the application. In general, the computing device 12 is connected to the power supply 22 and controls or sends a power signal to the electronic skin 26 to modify the skin as needed. Specifically the computing device 12 controls the power supply and only applies power to the skin 26 when skin change is required. Electric skin 26 can be a single monolithic unit that wraps around the medical device 28 or a plurality or a set of patches that attach and that are controlled individually. Therefore, when a patient leaves a room and a new patient arrives, the electric skin 26 on a medical device 28 in a room can be changed at the computing device 12 to provide new identifiers for the new patient. The computing device 12 can be located in the patient room or located remotely from the room. The computing device 12 is connected to the medical device 28 or caregiver or patient identification devices via a communication network that can be hard-wired, wireless or some combination thereof.

In operation, a hospital admits a plurality of patients. The algorithm 14 of the computing device 12 determines attributes unique to each patient and determines where similarities of attributes exist between patients. The algorithm 14 then determines a unique identifier or combination of identifiers associated with each patient depending on the similarity of attributes. The algorithm ensures that where similarities exist very distinct and unique identifiers are provided so that patients having similarities can be easily distinguished by human cognitive identifiers.

Once the algorithm 14 determines the human cognitive identifier for each patient the identifier is placed on a medium 26 in order to identify the patient. In one embodiment the medium 26 is an electronic skin such that the computing device 12 can be used to activate the electronic skin to generate the human cognitive identifier or combination of identifiers thereon.

In one embodiment, the computing device 12 can be used to activate electronic skins and identifiers on medical devices, caregivers and patients. The computing device 12 and algorithm 14 similarly can be used to identify caregivers associated with patients and/or medical devices in a room such as an operating room to provide human cognitive identifiers 16 for each caregiver authorized and associated with a particular patient or identify one or more medical devices 28 being used by a caregiver. Again, the algorithm 14 is able to choose distinctive identifiers so that similar medical devices 28 that are attached to an IV pole 30 together or plugged into a similar outlet 32 are easily identifiable by the caregivers. For example, the identifiers used on the electronic skins of the medical devices 28 can assist an anesthesiologist in identifying medical pumps they are using or are associated with and distinguish them from medical pumps a surgeon or nurse is using.

In another embodiment a first medical device 28 is associated with and connected to a first individual and a second medical device 28 is associated with and connected to a second individual. A separate, distinct medium 26 such as an electronic skin is placed on or associated with each of the first and second medical devices 28. In the embodiment using electronic skins, the electronic skins are in communication with a computing device 12 and in response to a control signal from the computing device 12 generate a combination of identifiers on each of the first medical device 28 and the second medical device 28 to indicate that the first individual and the second individual are associated.

Thus provided is a medical identification assembly that allows for a method of identifying individuals, medical devices and other medical items in a medical facility. The assembly is tailored to provide human cognitive identifiers 16 that minimize the chances of mistake by caregivers when providing medication, treatments and surgery for a patient. The system is efficient, easy to use and reusable. Because an electronic skin may merely be changed with the push of a button the need to customize medical devices and constantly replace devices to ensure safety is no longer necessary. The expenses of manufacturing or printing disposable or static tags, labels, badges and the like can be substantially reduced or eliminated. Adhesive tags or labels often lose adhesion over time and fall off. Temporary labels may not be current and accurate. Up-to-date, accurate and dynamic human readable visual associations and identifiers are provided by the present invention. Thus much expense is eliminated while the chance of mistake is decreased. Thus at the very least all the stated objectives have been met.

It will be appreciated by those skilled in the art that other various modifications could be made to the device, components, assemblies, systems and methods described above without departing from the scope of this invention. All such modifications and changes fall within the scope of the claims and are intended to be covered thereby.

What is claimed is:

1. A method of identifying a patient in a medical facility, the steps comprising:
   Sorting with an algorithm patient information received by a computing device;
   Identifying similarities of patient attributes;
   Selecting a combination of human cognitive identifiers associated with a patient with the algorithm in software of the computing device such that the selected combination of human cognitive identifiers has no similarity to identifiers of other patients having similar attributes;
   Placing the combination of human cognitive identifiers on at least one medium to identify the patient; and
   Placing the same human cognitive identifiers on a plurality of medical devices associated with the patient.

2. The method of identifying a patient of claim 1 wherein the combination of human cognitive identifiers are selected from a group consisting of shapes, colors, fonts, line pattern, icon, shading, symbols, background and border.

3. The method of identifying a patient of claim 1 wherein the combination of human cognitive identifiers are selected by the algorithm in software of the computing device by identifying attributes of a plurality of patients and selecting the combination of identifiers based on the attributes of the plurality of patients.

4. The method of identifying a patient of claim 1 wherein the medium is selected from the group consisting of a wrist band, badge, electronic skin, electronic medical record and prescription label.

5. The method of identifying a patient of claim 1 wherein the medium is an electronic skin on a medical device that is in communication with the computing device.

6. The method of identifying a patient of claim 5 wherein the electronic skin is electrically connected to the computing device to provide an electrical communication path.

7. The method of claim 1 wherein the computing device is selected from the group consisting of a central processing unit, a controller, a remote controller, a hand held device, a wired scanning device, a wireless scanning device, a barcode reader, and a radio frequency identifier.

8. The method of identifying a patient of claim 1 wherein identifiers are placed on a plurality of medium.

9. The method of identifying a patient of claim 8 wherein the computing device is electrically and operatively connected to each device that places the combination of identifiers on the plurality of medium.

10. The method of claim 8 wherein the plurality of medium are a plurality of electronic skins.

11. The method of claim 10 wherein the plurality of electronic skins are associated with a plurality of medical devices such that each medical device has a unique identifier.

12. The method of claim 10 wherein the plurality of electronic skins are associated with a plurality of caregivers such that each caregiver has a unique identifier.

13. The method of claim 10 wherein the plurality of electronic skins are associated with a plurality of patients such that each patient has a unique identifier.

14. The method of claim 11 wherein the plurality of medical devices are associated with a single patient.

15. The method of claim 12 wherein the plurality of caregivers are associated with a single patient.

16. The method of claim 11 wherein the plurality of electronic medical devices are associated with a single caregiver.

17. A medical identification assembly comprising:
   a computing device having software with an algorithm that:
      sorts through information associated with patients and caregivers;
      identifies similarities of patient and caregiver attributes;
      and determines a combination of identifiers associated with a patient or a caregiver;
   a medical device associated with the patient or caregiver wherein the combination of identifiers has no similarity to identifiers of other patients or caregivers having similar attributes;
   an electronic skin on the medical device and in communication with the computing device; and
   wherein said electronic skin generates the combination of identifiers in response to a control signal from the computing device to indicate that the medical device and the patient or caregiver are associated.

18. A medical identification assembly comprising:
   a computing device having software with an algorithm that sorts information associated with a patient or caregiver;
      identifies similarities of patient or caregiver attributes;
      and determines a unique combination of human cognitive identifiers associated with a patient wherein the combination of identifiers has no similarity to identifiers of other patients having similar attributes;
   a first medical device associated with and connected to the patient;
   a second medical device associated with and connected to a caregiver; and
   an electronic skin on each of the first medical device and the second medical device, the electronic skin being in communication with the computing device and in response to a control signal from the computing device generating the combination of identifiers on each of the first medical device and the second medical device to indicate that the patient and the caregiver are associated.

* * * * *